US 6,636,767 B1

(12) United States Patent
Knudson et al.

(10) Patent No.: US 6,636,767 B1
(45) Date of Patent: Oct. 21, 2003

(54) IMPLANATABLE STIMULATION DEVICE FOR SNORING TREATMENT

(75) Inventors: Mark B. Knudson, Shoreview, MN (US); Robert S. Nickoloff, St. Paul, MN (US); Timothy R. Conrad, Eden Prairie, MN (US)

(73) Assignee: Restore Medical, Inc., St. Paul, MN (US)

( * ) Notice: Subject to any disclaimer, the term of this patent is extended or adjusted under 35 U.S.C. 154(b) by 0 days.

(21) Appl. No.: 09/409,018

(22) Filed: Sep. 29, 1999

(51) Int. Cl.⁷ ............................................... A61N 1/08
(52) U.S. Cl. .................. 607/42; 128/848; 600/380; 607/134
(58) Field of Search ..................... 128/848, 850, 128/852, 859; 600/12, 13, 373, 380, 422, 423, 427, 534, 26; 607/42, 62, 65, 134, 48

(56) References Cited

U.S. PATENT DOCUMENTS

| | | |
|---|---|---|
| 3,998,209 A | 12/1976 | Macvaugh |
| 4,637,405 A * | 1/1987 | Brenman et al. ............ 128/787 |
| 4,830,008 A * | 5/1989 | Meer .......................... 128/421 |
| 4,978,323 A | 12/1990 | Freedman |
| 5,046,512 A | 9/1991 | Murchie |
| 5,052,409 A | 10/1991 | Tepper |
| 5,133,354 A | 7/1992 | Kallok |
| 5,158,080 A * | 10/1992 | Kallok ........................ 128/421 |
| 5,176,618 A | 1/1993 | Freedman |
| 5,178,156 A | 1/1993 | Takishima et al. |
| 5,190,053 A | 3/1993 | Meer |
| 5,212,476 A * | 5/1993 | Maloney ..................... 340/825 |
| 5,281,219 A | 1/1994 | Kallok |
| 5,284,161 A | 2/1994 | Karell |
| 5,456,662 A | 10/1995 | Edwards et al. |
| 5,514,131 A | 5/1996 | Edwards et al. |
| 5,540,733 A | 7/1996 | Testerman et al. |
| 5,591,216 A * | 1/1997 | Testerman et al. ............ 607/42 |
| 5,674,191 A | 10/1997 | Edwards et al. |
| 5,718,702 A | 2/1998 | Edwards |
| 5,792,067 A * | 8/1998 | Karell ........................ 600/534 |
| 5,843,021 A | 12/1998 | Edwards et al. |
| RE36,120 E | 3/1999 | Karell |
| 5,897,579 A | 4/1999 | Sanders |
| 5,922,006 A | 7/1999 | Sugerman |
| 5,979,456 A | 11/1999 | Magovern |
| 6,212,435 B1 * | 4/2001 | Lattner et al. ............... 607/134 |
| 6,240,316 B1 * | 5/2001 | Richmond et al. ............ 607/42 |

FOREIGN PATENT DOCUMENTS

| | | |
|---|---|---|
| EP | 0 706 808 A1 | 4/1996 |
| SU | 1553140 | 3/1990 |

OTHER PUBLICATIONS

Cole, P. et al., "Snoring: A Review and a Reassessment", *The Journal of Otolaryngology*, vol. 24, No. 5, pp. 303–306 (1995).

Dalmasso, F. et al., "Snoring: Analysis, Measurement, Clinical Implications and Applications", *European Respiratory Journal*, pp. 146–159 (1996).

Gillette, P. et al., "Pediatric Cardiac Pacing", *Cardiology Clinics*, vol. 10, No. 4, pp. 749–754 (Nov. 1992).

(List continued on next page.)

Primary Examiner—Jeffrey R. Jastrzab
Assistant Examiner—Frances P. Oropeza
(74) Attorney, Agent, or Firm—Merchant & Gould P.C.

(57) ABSTRACT

The present disclosure relates to methods and apparatuses for treating snoring by implanting a stimulating electrode into a patient. The electrode is placed in stimulating contact with an airway passage-controlling muscle of the patient. The electrode is energized to contract the muscle and alter the airway passage.

19 Claims, 3 Drawing Sheets

OTHER PUBLICATIONS

Harries, P. et al., "The Surgical Treatment of Snoring", *Journal of Laryngology and Otology*, vol. 110. 1105–1106 (Dec. 1996).

Huang, L. et al., "Biomechanics of Snoring", *Endeavour*, vol. 19, No. 3, pp. 96–100 (1995).

Schwartz, R. et al., "Effects of Electrical Stimualation to the Soft Palate on Snoring and Obstructive Sleep Apnea", *TheJournal of Prosthetic Dentistry*, vol. 76, No. 3, pp. 273–281 (Sep. 1996).

Wiltfant, J. et al., "First Results on Daytime Submandibular Electrostimulation of Suprahyoidal Muscles to Prevent Night–Time Hypopharyngeal Collapse in Obstructive Sleep Apnea Syndrome", *International Journal of Oral and Maxillofacial Surgery*, pp. 21–25 (1999).

Boot, H. et al., "Long–Term Results of Uvulopalatopharyngoplasty for Obstructive Sleep Apnea Syndrome", *The Laryngoscope*, pp. 469–475 (Mar. 2000).

Coleman, S. et al., "Midline Radiofrequency Tissue Reduction of the Palate for Bothersome Snoring and Sleep—Disordered Breathing: A Clinical Trail", *Otolaryngology—Head and Neck Surgery*, pp. 387–394 (Mar. 2000).

Fischer, Y. et al., "Die Radiofrequenzablation des weichen Gaumens (Somnoplastik)", *Redaktion*, pp. 33–40 (2000).

Kasey, K. et al., "Radiofrequency Volumetric Reduction of the Palate: And Extended Follow–Up Study", *Otolaryngology—Head and Neck Surgery*, vol. 122, No. 3, pp. 410–414 (Mar. 2000).

Ellis, P. D. M. et al., "Surgical relief of snoring due to palatal flutter: a preliminary report", *Annals of the Royal College of Surgeons of England*, vol. 75, No. 4, pp. 286–290 (1993).

Huang, L., "Flutter of Cantilevered Plates in Axial Flow", *Journal of Fluids and Structures*, vol. 9, pp. 127–147 (1995).

Dalmasso, F. et al., "Snoring: analysis, measurement, clinical implications and applications", *Euro Respir J.*, pp. 146–159 (1996).

Brochure, "Our Diagnostic Procedures are a Snap®!", *Snap Laboratories*, 4 pgs.

Brochure, "Snore–Free Nights—Guaranteed!", *Your Health News*, 2 pgs.

Brochure, "Snoreless™", *Nutrition for Life International*, 2 pgs. (Dec. 1999).

Brochure, "Haven't you suffered from Snoring long enough", *Somnoplasty$^{SM}$*, 2 pgs.

LaFrentz, J.R.L. et al., "Palatal stiffening techniques for snoring in a novel canine model", *ARO Abstracts*, vol. 22, Abstrct No. 499, pp. 125–126 (Feb. 13–18, 1999).

C. Lorenz, "If he Snores—what can you do about it?", Today's Woman, Jul. 1948, p. 112.

Search Report from PCT/US02/07966, mailed Nov. 8, 2002.

* cited by examiner

IMPLANATABLE STIMULATION DEVICE FOR SNORING TREATMENT

BACKGROUND

1. Field of the Invention

This invention is directed to method and apparatus for treating snoring.

2. Description of the Prior Art

Snoring has received increased scientific and academic attention. One publication estimates that up to 20% of the adult population snores habitually. Huang, et al., "Biomechanics of Snoring", *Endeavour*, Vol. 19, No. 3, pp. 96–100 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress). Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge comprises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Alternatively, these devices must be used during the day for a period of time causing disruption of daily activity, interference with daily life. This may generally be assumed to cause them to be prone to a significant risk of non-compliance by the wearer. Such devices, though have met with some success in treating disorders such as snoring and Obstructive Sleep Apnea.

SUMMARY OF THE INVENTION

According to a preferred embodiment of the present invention, a method and apparatus are disclosed for treating snoring of a patient. The invention includes implanting a stimulating electrode into a patient. The electrode is placed in stimulating contact with an airway passage-controlling muscle of the patient. The electrode is energized to contract the muscle and alter the airway passage.

DESCRIPTION OF THE PREFERRED EMBODIMENT

For ease of understanding the present invention, the dynamics of snoring are explained with reference to FIGS. 1–5. The hard palate HP overlies the tongue T and forms the roof of the mouth M. The hard palate HP includes a bone support B and does not materially deform during breathing. The soft palate SP is soft and is made up of mucous membrane, fibrous and muscle tissue extending rearward from the hard palate HP. A leading end LE of the soft palate SP is anchored to the trailing end of the hard palate HP. A trailing end TE of the soft palate SP is unattached. Since the soft palate SP is not structurally supported by bone or hard cartilage, the soft palate SP droops down from the plane of the hard palate HP in an arcuate geometry of repose.

Figures 1, 2:
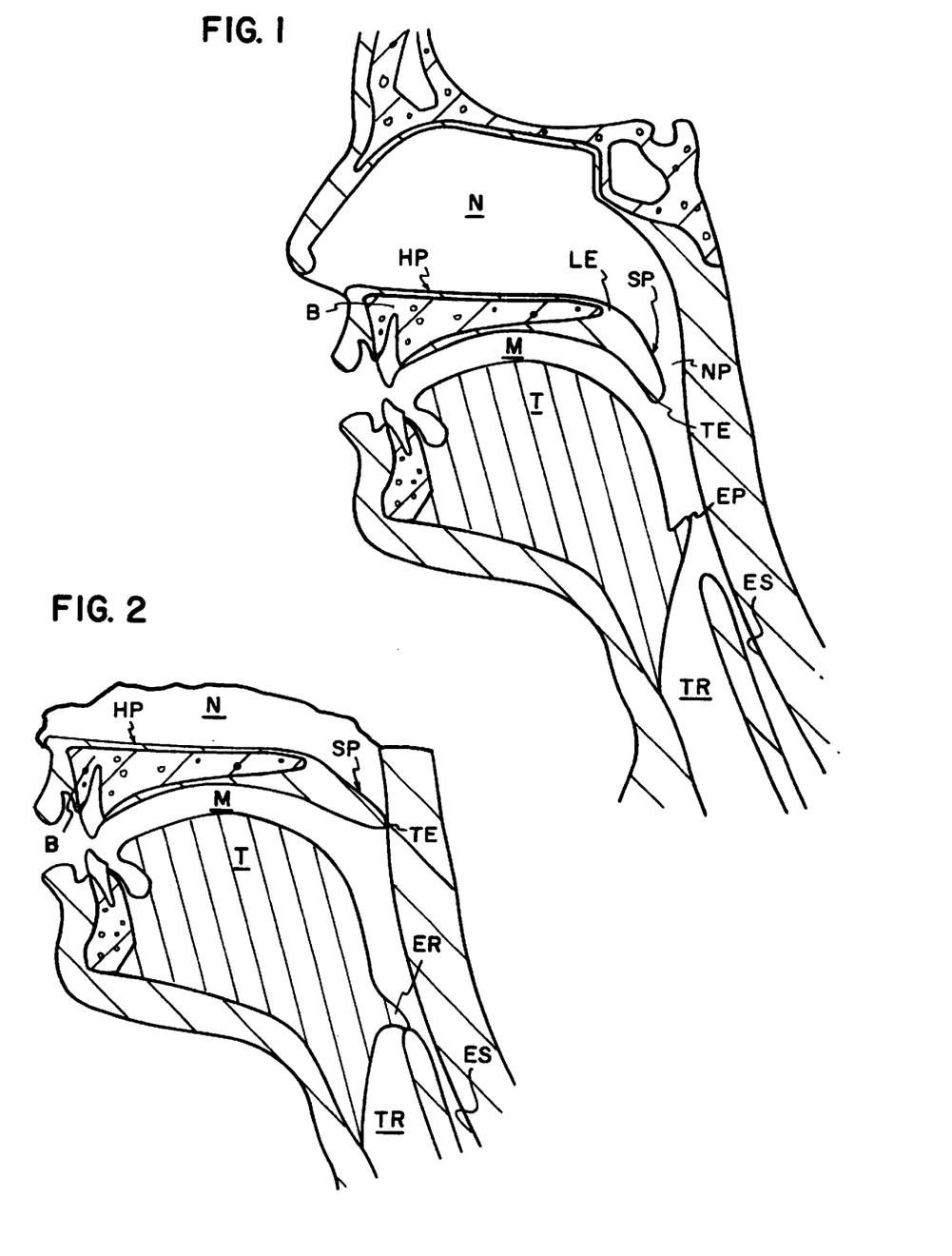
FIG. 1 is a side sectional view of a portion of a human head showing a soft palate in a relaxed state and in relation in adjacent anatomical features.
FIG. 2 is a portion of the view of FIG. 1 showing the soft palate in a flexed state.

The pharyngeal airway passes air from the mouth M and the nasal passages N into he trachea TR. The portion of the pharyngeal airway defined between opposing surfaces of the upper surface of the soft palate SP and the wall of the throat is the nasopharynx NP.

During normal breathing, the soft palate SP is in the relaxed state shown in FIG. 1 with the nasopharynx NP unobstructed and with air free to flow into the trachea TR from both the mouth M and the nostrils N.

During swallowing, the soft palate SP flexes and extends (as shown in FIG. 2) to close the nasopharynx NP thereby preventing fluid flow from the mouth M to the nasal passages N. Simultaneously, the epiglottis EP closes the trachea TR so that food and drink pass only into the esophagus ES and not the trachea TR. The soft palate SP is a valve to prevent regurgitation of food into the nose N. The soft palate SP also regulates airflow through the nose N while talking. Since the soft palate SP performs such important functions, prior art techniques for surgically altering the soft palate SP can compromise these functions.

The majority of snoring is caused by the soft palate SP flapping back and forth. If breathing is solely through the nose N with the mouth closed, the trailing edge TE of the soft palate SP is sucked into the nasopharyngeal space NP obstructing the airway and subsequently falls opening the airway in a repeating cycle. When the mouth is open, air flows over the upper and lower surfaces of the soft palate SP causing the soft palate SP to flap up and down alternating in obstructing the oral and nasal passageways M, N. The snoring sound is generated by impulses caused by rapid obstruction and opening of airways. Huang, et al., state in the airway passage opening and closing occurs 50 times per second during a snore. Huang, et al., utilizing a spring-mass model (FIG. 5) to illustrate oscillation of the soft palate in response to airflow (where the soft palate is the ball B of mass depending by a spring S from a fixed anchor A).

Figure 3:
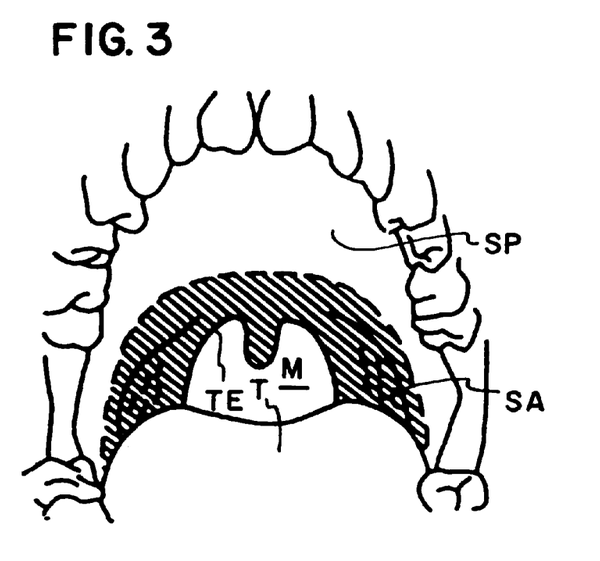
FIG. 3 is a front view of an interior of the mouth shown in FIG. 1 and showing an area to be ablated according to a first prior art surgical procedure.
Figure 4:
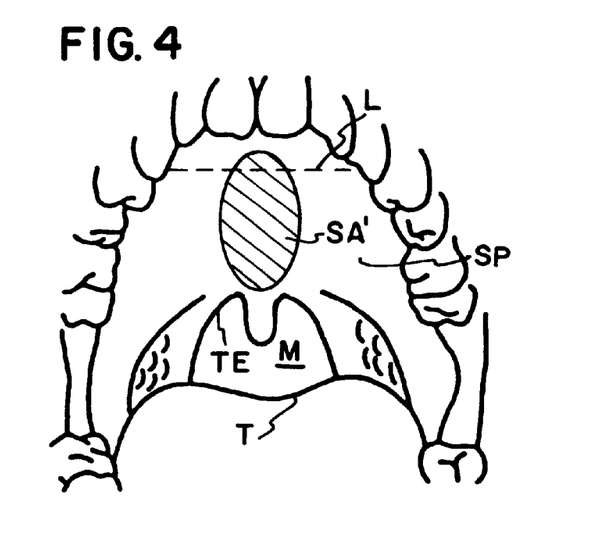
FIG. 4 is the view of FIG. 3 and showing an area to be scarred according to a second prior art surgical procedure.
Figure 5:
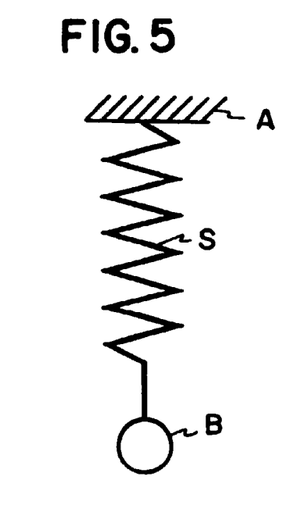
FIG. 5 is a schematic representation of a spring-mass system model of the soft palate.

Huang, et al., analogize the shortening of the soft palate SP in uvulopalatopharyngoplasty as effectively raising the critical air flow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

The present invention is directed to a method and apparatus for altering the dynamic response of the soft palate by altering airflow past the soft palate. With reference to the spring-mass model (FIG. 5), the soft palate is moved by airflow. Airflow through an orifice varies in response to the orifice size. The present invention alters the size of the air passage through a minimally invasive surgical implant to allow stimulation of airway defining muscles of the oropharynx (i.e., mouth and throat).

The present invention stimulates muscles of one or more of the soft palate SP, tongue T and back of the throat. In the soft palate SP, these muscles include, but are not limited to, the Levator veli paltini, the dextera, the Palatopharyngeous and the Palatoglossus muscles. At the back of the throat, these muscles include, but are not limited to, the Superior, Middle and Inferior pharyngeal constrictor, the Salpingopharyngeous and the Stylopharyngeous muscles. In the tongue T, these muscles include, but are not limited to, the Genioglossus and Geniohyoid muscles.

Stimulating the muscles of the soft palate, tongue and throat is intended to alter the dynamic response of the soft palate to airflow. Namely, stimulation of the soft palate SP causes the soft palate to move away from the tongue T, stimulation of the tongue T causes the tongue T to move away from the soft palate SP, and stimulation of the back of the throat causes the throat to move rearwardly. Alone or in combination, these actions increase the size of the airway thereby decreasing air velocity and the disrupting force which would otherwise cause oscillation of the soft palate SP.

Figure 6:
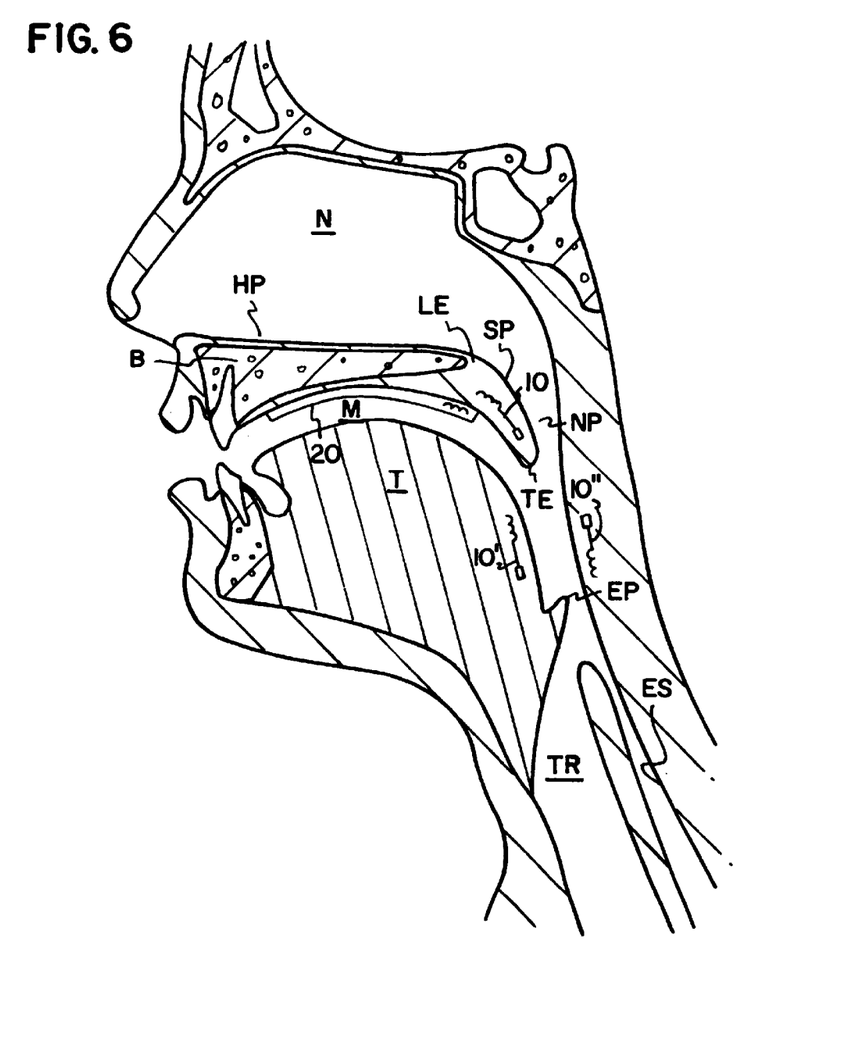
FIG. 6 is the view of FIG. 1 showing electrodes placed in the muscles of the soft palate, tongue and throat.

Stimulation of the muscles is accomplished by implanted electrodes 10, 10' and 10" placed in the airway passage-defining muscles (identified above) of the soft palate SP, tongue T and back of throat (as illustrated in FIG. 6). Implantable muscle stimulating electrodes are well known and may be such as those used in cardiac pacing.

The implant 10, 10', 10" can be positioned and stimulated in a plurality of ways to alter the shape of the airway, to change the dynamic response of the airway tissues or a combination of both. Unlike the prior art surgical techniques, the electrodes 10, 10', 10" that will be described are easy to insert in a small incision resulting in reduced patient discomfort and are not exposed to the interior of the mouth (such as the surface scarring of Huang, et al.) as a patient irritant. Also, as will be described, the degree of dynamic remodeling and stimulation pattern can be fine tuned avoiding the need for excessive anatomical modification and are reversible in the event of adverse consequences.

The present invention permits the surgeon to apply stimulation to various muscles until the desired alteration in airway area and tone is achieved so that snoring inducing oscillation is abated at normal airflow. The individual electrodes 10, 10', 10" may be placed into the soft palate, tongue or throat muscles through small individual incisions closed by sutures which is much less traumatic than the gross anatomical destruction of uvulopalatopharyngoplasty or the large surface area scarring proposed by Huang, et al.

A control device 20 is provided for controlling the electrodes 10, 10', 10". The control device 20 is shown as a removable appliance (schematically shown in FIG. 6 with it being appreciated that appliances for placement in the mouth are well known) which fits the form of the hard palate or sub-lingual spaces.

The control device 20 is electrically coupled to the electrodes 10, 10', 10" through electromagnetic coupling which avoids the need for electrode leads being exposed from the implants 10, 10', 10". Specifically, the electrode 10 (shown in FIG. 7 and it being appreciated that electrodes 10', 10" are of similar construction) includes a pacing electrode 12 for stimulating muscle in response to a signal through the electrode 10. Leads 14 connect the pacing electrode 12 to an inductive winding 16. In use, the entire electrode 10 (i.e., each of the components of the pacing electrode 12, leads 14 and winding 16) are imbedded in the patient and not exposed.

Figure 7:
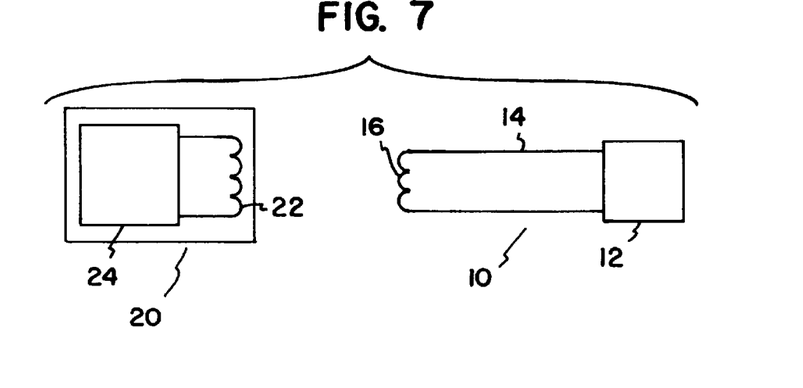
FIG. 7 is a schematic representation of a pacing electrode inductively coupled to a control device.

The control device 20 is shown schematically and includes an inductive winding 22 connected to a control circuit 24. Control circuit 24 is only shown schematically. Control circuits for pacing electrodes are well known and widely used in cardiac pacing. In the present invention, preferably none of the components of the control device 20 (i.e., the winding 22 and circuit 24) are implanted. Instead, preferably such components are contained in the removable oral appliance control device 20 although some elements (e.g., a battery may be worn externally by the patient).

The control winding 22 is positioned on the control device 20 to be inductively coupled to the electrode winding 16 when the control device 20 is in place. In the event multiple electrodes 10, 10', 10" are placed in multiple muscles, the control device 20 may contain a plurality of windings 22 each uniquely tuned to the windings of the electrodes 10, 10", 10" such that each electrode 10, 10', 10" may be uniquely paced. Also, each of the electrodes 10, 10', 10" can be provided with filter circuits to pass only desired signals to the pacing electrodes.

The control device 20 sends a pulsitile signal to the electrode 10 through the inductive coupling of windings 16 and 22. In response, the electrode 10 causes pacing contraction of the muscle. Preferably, the pacing is selected to contract the muscle up to and including tetanic contraction.

With the present invention, the muscle is contracted to increase the size of the airway and reduce palatal flutter. The amount of pacing can be tuned to the unique physiology of the patient. The control device need only be used during sleep. It is anticipated that regular use of the control device 20 results in improved tone of the paced muscles reducing or eliminating future need to use the control device 20. Unlike the appliances of U.S. Pat. Nos. 5,284,161 and 5,792,067, the present device has more effective pacing since muscles are being paced directly by implanted electrodes rather than through less efficient surface stimulation. Further, the present invention contemplates pacing of all muscles defining the airway passage and not just the soft palate.

Having described the invention, alternatives and embodiments may occur to one of skill in the art. It is intended that such modifications and equivalents shall be included within the scope of the following claims.

What is claimed is:

1. A method for treating snoring comprising:
   implanting at least first and second stimulating electrodes into a patient with said electrodes in stimulating contact with at least first and second different airway passage-controlling muscles, respectively, of said patient;
   electrically coupling said first and second electrodes to a controller contained within an appliance sized to be removably placed within a mouth cavity of said patient, said controller containing at least first and second windings, each winding uniquely tuned to windings of said first and second electrodes; and
   energizing and uniquely pacing said first and second electrodes to contract said muscles and alter said airway passage, wherein said controller is electrically coupled to said electrodes when said appliance is placed within said mouth cavity.

2. A method according to claim 1 wherein slid electrodes are energized by electrically coupling said electrodes through an electromagnetic field to said controller.

3. A method according to claim 1 wherein one of said muscles is a muscle of the soft palate.

4. A method according to claim 1 wherein one of said muscles is a muscle of the tongue.

5. A method according to claim 1 wherein one of said muscles is a muscle of the pharynx.

6. A method according to claim 3 wherein said muscle is selected from at least one of the Levator veli paltini, the Palatopharyngeous and the Palatoglossus muscles.

7. A method according to clam 4 wherein said muscle is selected from at least one of the Genioglossus and Geniohyoid muscles.

8. A method according to claim 5 wherein said muscle is selected from at least one of the Superior, Middle and inferior pharyngeal constrictor, the Salpingopharyngeous and the Stylopharyngeous muscles.

9. An apparatus for treating snoring of a patient, said apparatus comprising:
   two or more stimulating electrodes adapted to be implanted into a patient with said electrodes in stimulating contact wit at least one two or more different airway passage-controlling muscles of said patient; and
   a control member for energizing and uniquely pacing said electrodes to contract said muscles and alter said airway passage, said control member containing two or more windings, each winding uniquely tuned to windings of said two or more electrodes wherein said control member is carried on an appliance adapted to be removably placed, non-invasively in a mouth of said patient.

10. An apparatus according to claim 9 wherein said windings of said electrodes and said control member cooperate to inductively couple said control member and said electrodes.

11. The method of claim 1 wherein said first and second airway passage-controlling muscles are selected from the group consisting of the soft palate, the tongue, and the pharynx.

12. A method for treating snoring comprising:
   implanting at least first and second stimulating electrodes into a patient with said electrodes in stimulating contact with at least one airway passage-controlling muscle of said patient, wherein said muscle is a muscle of the soft palate or the pharynx; and
   energizing and uniquely pacing said first and second electrodes to contract said muscle and alter said airway passage, wherein said first and second electrodes are uniquely tuned and uniquely paced.

13. The method of claim 12 wherein said first electrode is implanted in a first airway passage-controlling muscle and said second electrode is implanted in a second airway passage-controlling muscle, wherein said first and second muscles are different.

14. A method for treating snoring comprising:
   implanting at least first and second stimulating electrodes into a patient with said electrodes in stimulating contact with e at least first and second different airway passage-controlling muscles respectively, of said patient wherein said airway passage-controlling muscles are muscles of the soft palate or pharynx; and
   energizing said electrodes to contract said muscles and alter said airway passage;
   wherein said electrodes are energized by electrically coupling said electrodes through an electromagnetic field to a controller not implanted in said patient;
   wherein said controller is contained within an appliance sized to be removably placed within a mouth cavity of said patient and with said controller electrically coupled to said electrodes when said appliance is placed within said mouth cavity.

15. A method according to claim 14 wherein one of said muscles is selected from at least one of the Levator veli paltini, the Palatopharyngeous and the Palatoglossus muscles.

16. A method according to claim 14 wherein one of said muscles is selected from at least one of the Superior, Middle and Inferior pharyngeal constrictor, the Salpingopharyngeous and the Stylopharyngeous muscles.

17. An apparatus for treating snoring of a patient, said apparatus comprising:
   a stimulating electrode adapted to be implanted into a patient with said electrode in simulating contact with an airway passage-controlling muscle of said patient; and a controller for energizing said electrode to contract said muscle and alter said airway passage;

wherein said controller is cared on an appliance adapted to be removably placed, non-invasively in mouth of said patient;

wherein said controller and said electrode interface dough an inductive coupling provided when the controller is in the patient's mouth.

18. An apparatus according to claim 17, wherein said appliance is an oral appliance adapted to fit the form of the hard palate or sub-lingual spaces of the patient's mouth.

19. An apparatus for treating snoring of a patient, said apparatus comprising:

a stimulating electrode adapted to be implanted into a patient with said electrode m stimulating contact with an airway passage-controlling muscle of said patient; and a controller for energizing said electrode to contract said muscle and alter said airway passage;

wherein said controller is carried on an appliance adapted to be removably placed, non-invasively in mouth of said patient;

wherein said controller and said electrode are electrically coupled through a leadless interface provided when the controller is in the patient's mouth.

\* \* \* \* \*

UNITED STATES PATENT AND TRADEMARK OFFICE

CERTIFICATE OF CORRECTION

PATENT NO. : 6,636,767 B1
DATED : October 21, 2003
INVENTOR(S) : Knudson et al.

It is certified that error appears in the above-identified patent and that said Letters Patent is hereby corrected as shown below:

Title page,
Item [54], Title, "IMPLANATABLE STIMULATION DEVICE FOR SNORING TREATMENT" should read -- IMPLANTABLE STIMULATION DEVICE FOR SNORING TREATMENT --
Item [56], References Cited, OTHER PUBLICATIONS, "Wiltfant," should read -- Wilfang, --

Column 2,
Line 66, "N into he" should read -- N into the --

Column 5,
Lines 3-4, "windings of the electrodes 10, 10", 10" such" should read -- windings of the elctrodes 10, 10', 10" such --
Line 49, "wherein slid" should read -- wherein said --
Lines 65-66, "and inferior" should read -- and Inferior --

Column 6,
Line 5, "contact wit at least one two or more" should read -- contact with two or more --
Line 41, "with e at least" should read -- with at least --
Lines 42-43, "said patient wherein" should read -- said patient, wherein --
Line 66, "in simulating contact" should read -- in simulating contact --.

Column 7,
Line 3, "is cared on" should read -- is carried on --
Line 6, "interface dough" should read -- interface through --

UNITED STATES PATENT AND TRADEMARK OFFICE
CERTIFICATE OF CORRECTION

PATENT NO.   : 6,636,767 B1
DATED        : October 21, 2003
INVENTOR(S)  : Knudson et al.

It is certified that error appears in the above-identified patent and that said Letters Patent is hereby corrected as shown below:

Column 8,
Line 2, "electrode m" should read -- electrode in --

Signed and Sealed this

Thirty-first Day of August, 2004

JON W. DUDAS
*Director of the United States Patent and Trademark Office*